United States Patent [19]

Farolfi et al.

[11] Patent Number: 4,937,079

[45] Date of Patent: Jun. 26, 1990

[54] PHARMACEUTICAL COMPOSITION FOR THE PROPHYLAXIS AND THERAPY OF GASTRIC ULCER

[75] Inventors: Giancarlo Farolfi, Como; Giovanni Gazzani, Appiano Gentile; Riccardo Niada, Varese; Marisa Mantovani, Villa Guardia, all of Italy

[73] Assignee: Crinos Industria Farmacobiologica SpA, Coma, Italy

[21] Appl. No.: 138,400

[22] Filed: Dec. 28, 1987

[30] Foreign Application Priority Data

Jan. 12, 1987 [IT] Italy ............................... 19048 A/87

[51] Int. Cl.⁵ .................. A61K 9/14; A61K 9/20; A61K 37/10
[52] U.S. Cl. ............................... 424/485; 424/488; 424/489; 424/464; 424/480; 514/8
[58] Field of Search ............... 424/78, 464, 468, 470, 424/500, 488, 485, 489, 480; 514/8

[56] References Cited

U.S. PATENT DOCUMENTS 3,926,921 12/1975 Butti et al. .............................. 514/8
3,961,045 1/1976 Wurzburg et al. .................... 424/78
4,151,276 4/1979 Caulin et al. ......................... 424/111

FOREIGN PATENT DOCUMENTS 2007475 1/1970 France ................................. 424/78
1179384 1/1970 United Kingdom .
1249907 10/1971 United Kingdom .

OTHER PUBLICATIONS

1-Pharmacology, vol. 104, 1986, p. 53, 104:61857x; Effect of Sulglycotide on Gastric Bicarbonate Secretion in Humans.

Chemical Abstracts, vol. 100, 1984, p. 38, 100:61608j; Sulglycotide Displays Cytoprotective Activity in Rat Gastric Mucosa.

*Primary Examiner*—Joseph L. Schofer
*Assistant Examiner*—Carmien B. Pili-Curtis
*Attorney, Agent, or Firm*—Armstrong, Nikaido, Marmelstein, Kubovcik & Murray

[57] ABSTRACT

The combination of a hydrophilic polymer with sulglycotide in pharmaceutical compositions for orally use enhances the anti-ulcer activity of sulglycotide.

7 Claims, No Drawings

PHARMACEUTICAL COMPOSITION FOR THE PROPHYLAXIS AND THERAPY OF GASTRIC ULCER

The present invention relates to a pharmaceutical composition useful for the prophylaxis and therpay of gastric ulcer.

The importance of gastric ulcer as a therapeutical problem does not need comments: it is enough to remember that in the last 10 years important drugs have been invented and developed, such as cimetidine and ranitidine, having this main activity.

Parallely to the development of new drugs huge has been the research effort dedicated to the investigation of the causes and of the mechanisms involved in this pathology.

These researches, of essentially pharmacological character, are based on experiments in which the activity of the drug is evaluated with respect to the effectiveness shown in preventing the occurrence of the experimentally induced ulcer.

A number of studies has been recently aimed at the evaluation of the drugs which are today used in sucha pathology in order to assess whether they would be capable of giving place to a protection of the gastric mucosae, in the presence of necrotizing agents, in an experimental model in which the gastric acid secretion would remain unchanged. This experimental model has been suggested by Robert (A. Robert et al. "Cytoprotection by prostaglandins in rats" Gastroenterol. 77 443–443, 1979) in order to demonstrate that the prostaglandins were active in protecting the gastric mucosaae from lesions or necrosis, localized in the secreting portion of the stomac, as induced from several substance, (absolute ethanol, 0.2N NaOH, 0.6N HCl, 25% NaCl, boiling water). This effect however was not related to the inhibition of the acid secretion; in fact anticholinergic drugs (methscopolamine bromide) or anti-$H_2$ drugs (cimetidine) or even anti-acidic drugs (sodium bicarbonate), if administered in an uniqu dose were not active in preventing the lesions. These unexpected results stimulated the prosecution of studies aiming to assess the effectiveness in the same tests of other drugs used in this pathology, also in order to clarify the possible connections to mediating substances (the prostaglandins) supposedly involved in such a mechanism of defence of the gastric mucosae.

It has been demonstrated that after only one dose of both ranitidine (A. Tarnasky, "Comparison of antacid, sucralfate, cimetidine and ranididine in protection of astric mucosa ethanol injury" Gastroenterology 84, 1331 1983) and atropine (J. Puurunen et al., "Effect of prostaglandin E2, cimetidine and atropine on ethanol induced mucosal damage in the rat," Scand. J. Gastroenterol. 15, 484–488 1950) are not active; on the contrary active are sucralfate (A. Tarnawsky, same above cited paper), carbenoxolone (BY. C. Wan, "Cytoprotective action of carbenoxolone sodium on ethanol-induced gastric lesions in rats and its inhibition by indomethacin", J. Pharm. Pharmacol., 37, 739–741, 1985) and under some aspects also piranzepine (E. Trabucchi et al. "Cytoprotection by PGE2, piranzepine or vagotomy; a transmission and scanning microscope electron microscope study in rats," Pharm. Res. Comm., 18, 357–369, 1986).

The results of these subsequent experiments, thus, just confirmed the observations of Robert as regards the lack of whatever activity in a such test of the anti-$H_2$ anti-acid and anti-cholinergic products.

By the way these data are not in opposition with the proved pharmacological and clinical efficacy of these drugs. More simply, the Robert's test does not foresee that the acidic gastric secretion is the factor inducing the ulcer, as it occurs in other tests, such as for instance the Shay ulcer.

The subject experimental model does reveal the activity of those drugs acting through a different mechanism in the ulcer pathology, namely by enhancing the endogenic mechanisms of protection of the gastric mucosa, such as carbenoxolone and sucralfate, the clinical activity of which in the ulcer therapy has been widely evidenced and acknowledged. It is moreover to be added that the latter approach to this therapeutical problem is of relevant importance with respect to the possibility of preventing the ulcer formation, which normally is the subsequent and final step of the pathology known as "non ulceric dyspepsia".

As it is known from the medical science, the non ulceric dyspepsia has the same symptomatology of the true ulcer, from which it can be however distinguished through the stomac exploration by endoscopic route.

In this case the anti-$H_2$ and the anti-acid drugs have been in fact found devoid of efficacy (P. Lance et Al., "A controlled clinical trial of cimetidine for the treatment of non-ulcer dyspepsia" J. Clin. Gastroent., 8, 414–8, 1986; J. M. B. Saunders et Al., "Dyspepsia: incidence of non-ulcer disease in a controlled trial of ranidi-tine in general practice" Brit. Med. J., 292, 665–9, 1986; O. Nyren et Al. "Absence of therapeutic benefits fro antacids or cimetidine in non-ulcer dyspepsia" New England J. Med., 314, 6, 339–343, 1986; Editorial Notes in the Lancet 1306–7, 1986).

These results, very probably, are to be related to the fact that most of the subjects, which later on are involved in the true ulceric pathology, have a normal gastric secreting activity, whereas only a minor part can be properly defined as "hipersecretors" (J. P. Horrocks et al., "Clinical presentation of patients with dyspepsia. Detailed Symptomatic study of 360 patients" Gut, 19, 19–26, 1978; K. M. Mollman et Al. "A diagnostic study of patients with upper abdominal pain" Scand. J. Gastroenterol., 10, 805–9, 1975).

The sulglycotide (D.C.I. OMS liste No. 13, Chronique OMS 27–10 1973) is a macromolecule obtained through direct sulfonation of a glycopeptide extracted from the gastric or duodenal mucosa of swine (U.K. Patent 1,249,907) and is used since several years in the prophylaxis and therapy of the gastric and duodeneal ulcer.

This drug, already tested several years ago with success in a number of models of experimental ulcer (G. Prino et Al., "Inhibition of experimentally induced gastric ulcers in the rat by a new sulfated glycopeptide", Eur. J. Pharmacol., 15, 119–126 1971) did not show a satisfactory activity in the Robert's model (R. Niada et al. "Cytoprotection by sulglycotide; prevention of gastric necrosis in rat" "Pharm. Res Comm., 13, 695–704, 1981).

As a matter of fact for the sulglycotide it had not been possible to demonstrate a protecting activity towards the gastric mucosa having the same efficacy as carbenoxolone or sucralfate; in fact, whereas the activity of these two drugs was evident after only one administration, for the sulglycotide five administrations were necessary, repeated every 24 hours from each other. The doses were of between 25 and 200 mg/kg. More particularly, according to these results, it was not to be expected that sulglycotide, for instance, might be a pharmacological agent useful in the non ulceric dyspepsia as previously discussed as regards the causes and the rationale on which the therapy is based.

Among the pharmaceutical forms the oral ones are the more widespread with relation to their easy taking, pleasant taste and easy carrying. Moreover they are evidently advantageous for the manufactured owing to their easy and economic preparation.

For these formulations the use of hydrophilic polymers is known as density enhancers and to prepare suitable suspensions of compounds not soluble in aqueous medium, or as stabilizers for the emulsions.

These substances can moreover be used as binders and as disgregating agents in the preparation of tablets (for examples, polyvinylpyrrolidone, sodium carboxymethylcellulose).

According to Remington's Pharmaceutical Sciences 16$^{th}$ Ed., 1980 (Mack Publishing Company) the hydrophilic polymers can be grouped in three basic classes:

natural polymers, such as for instance locust gum, agar-agar, guar gum, pectin, sodium alginate, xantan gum, carregeenin;

cellulose derivatives such as for example methyl cellulose, hydroxy ethyl cellulose, hydroxy propyl cellulose;

synthetic polymers such as for example polyvinylpyrrolidone.

Among these substances moreover the pectin is used in the treatment of the children diarrhea owing to its properties of intestinal absorber. It has been now surprisingly found and is the subject of the present invention that by combining the sulglycotide with at least one the above mentioned polymers the anti-ulcer activity of the drug is enhanced according to the test of Robert and consequently the sulglycotide in this type of combination and composition shows a significant gastroprocting effect even after only one administration.

This effect is particularly worth of noticing if it is considered that besides the tested an unefficacy of this active principle according to this posologic scheme, which is by the way confirmed from the results reported in the table I, also the hydrophilic polymers under consideration are devoid, under the same conditions of whatever activity.

The data reported in the table I have been obtained by inducing ulcer through the administration of ethanol (1 ml) to the rat three hours after the single adminstration per os at the doses, relating to the tested substances, which are reported in the same table.

The animals were sacrificed 5 hours after the ethanol administration. The stomac was then removed and was opened at the big bend.

The mucosa was then examined and a core was given to the necrotic lesions depending on their heaviness.

TABLE I

Ethanol induced ulcer effects of some hydrophilic polymers and of the sulglycotide, administered only one time three hours before the ethanol.
Average value ± Standard Error of 16 data per group.

| Substance | Dose mg/kg p.o. | Gastric lesions (score) | Protection % vs H$_2$O |
|---|---|---|---|
| H$_2$O | 10 ml/kg | 4.12 ± 0.31 | — |
| methylcellulose | 185 | 3.78 ± 0.26 | 8.25* |
| pectin | 340 | 3.87 ± 0.26 | 6.07* |
| thragacant gum | 300 | 3.84 ± 0.26 | 6.80 |

TABLE I-continued

Ethanol induced ulcer effects of some hydrophilic polymers and of the sulglycotide, administered only one time three hours before the ethanol.
Average value ± Standard Error of 16 data per group.

| Substance | Dose mg/kg p.o. | Gastric lesions (score) | Protection % vs H$_2$O |
|---|---|---|---|
| H$_2$O | 10 ml/kg | 3.94 ± 0.15 | — |
| sulglycotide | 200 | 3.53 ± 0.24 | 10.41* |

*Statistically non-significant protection (ANOVA, Tukey Test).

The particular hydrophilic polymers to which reference is made in this table and in the following one are to be meant as reported only for example and non in limiting sense as regards the substances belonging to this class which can be used for the purposes to be attained with the present invention.

The following table II illustrates the results obtained in the same test by using the corresponding mixtures, (referred to in the following formulation examples) with the sulglycotide of the hydrophilic polymers of the table I, and at the same doses reported herein.

TABLE II

Ethanol induced ulcer protecting effects of the sulglycotide combined with several hydrophilic polymers, administered only one time three hours before ethanol.
Average values ± Standard Error of 20 data for group.

| Substance | Dose mg/kg p.o. | Gastric lesions (score) | Protection % vs H$_2$O |
|---|---|---|---|
| H$_2$O | 10 ml/kg | 4.60 ± 0.17 | — |
| sulglycotide (A) + methylcellulose (B) | A = 200 B = 185 | 3.15 ± 0.31* | 31.52 |
| sulglycotide (A) + pectin (B) | A = 200 B = 340 | 2.27 ± 0.24* | 50.65 |
| sulglycotide (A) + thragacant gum (B) | A = 200 B = 300 | 3.02 ± 0.31* | 34.35 |

*P <0.01 (ANOVA, Tukey test).

It has been moreover assessed that the sulglycotide in such a combination shows in the test of Robert an activity which is proportional to the administered dose.

A gel pharmaceutical form containing several increasing amounts of sulglycotide according to the formulations foreseen in the examples 1A–1C, has been tested against the corresponding placebo and against sulglycotide alone (400 mg/kg dose) in the ethanol induced ulcer test and in the NaOH induced ulcer test.

The gel volumes were 10 ml/kg. In the case of the NaOH induced ulcer the formulations according to examples 1A–1C were diluted in the ratio 1:1 before the experiment.

TABLE III

Ethanol induced ulcer effects of sulglycotide in gel administered only one time at different doses (formulations 1A–1C) 3 hours before ethanol. Under the same experimental conditions also sulglycotide alone and the placebo were tested. Average values ± Standard Error of 18 data per group.

| Substance | Dose mg/kg p.o. | Gastric lesions (score) | Protection % vs H$_2$O |
|---|---|---|---|
| distilled H$_2$O | 10 ml/kg | 3.94 ± 0.15 | — |
| placebo gel | 10 ml/kg | 3.53 ± 0.18 | 10.41 |
| sulglycotide gel (ex. 1A) | 100 | 3.06 ± 0.29 | 22.23 |
| sulglycotide gel (ex. 1B) | 200 | 2.17 ± 0.32* | 44.92 |
| sulglycotide gel (ex. 1C) | 400 | 1.25 ± 0.30§ | 68.27 |
| sulglycotide in H$_2$O | 400 | 3.53 ± 0.24 | 10.41 |

*P <0.01 (Anova Tukey test)

The calculatedd ED$_{50}$ was 403.09 (299.05–507.13)mg/kg p.o.

TABLE IV

NaOH induced ulcer effects of sulglycotide in gel administered only one time at different doses (formulations 1A–1C) three hours before NaOH. Under the same experimental conditions also sulglycotide alone and placebo were tested.
Average values ± Standard Error 18 data per group.

| Substance | Dose mg/kg p.o. | Gastric lesions (score) | Protection % vs H$_2$O |
|---|---|---|---|
| distilled H$_2$O | 10 ml/kg | 3.73 ± 0.21 | |
| placebo gel | 10 ml/kg | 3.26 ± 0.31 | 12.60 |
| sulglycotide gel (ex. 1A) | 50 | 2.40 ± 0.32 | 35.66 |
| sulglycotide gel (ex. 1B) | 100 | 1.13 ± 0.16* | 69.70 |
| sulglycotide gel (ex. 1C) | 200 | 0.70 ± 0.19* | 81.23 |
| sulglycotide in H$_2$ | 400 | 3.73 ± 0.27 | 0 |

*P <0.01 (Anova Tukey test)

The calculated ED$_{50}$ was 40.5 (31.2–52.4) mg/kg p.o.

As it is evident from the tables III and IV, the activity of sulglycotide in both experimental conditions is highly significant and depending on the dose if the substance is combined with hydrophilic polymers.

In both cases, in fact, it has been possible to calculate the corrisponding value of ED$_{50}$.

The sulglycotide alone, even at the dose of 400 mg/kg, is devoid of activity.

Lastly it is been assessed whether in the test under consideration the hydrophilic polymers were able to act in the same sence on the activity of other gastroprotecting drugs.

As an example the sucralfate has been selected, which has been tested in the rat both alone and in admixture with pectin.

The results obtained are reported in the table V. The experimental scheme was the same of the ethanol induced ulcer and the administered volume was 10 ml/kg.

TABLE V

Ethanol induced ulcer-effect of sucralfate and pectin, sucralfate alone and pectin alone administered only one time before the ethanol. Average ± Standard Error of 20 data per group (16 data for the sucralfate alone).

| Substance | Dose mg/kg p.o. | Gastric lesions (score) | Protection % vs H$_2$O |
|---|---|---|---|
| H$_2$O | 10 ml/kg | 4.55 ± 0.14 | — |
| pectin | 340 | 4.30 ± 0.21 | 5.49 |
| sucralfate (A) + pectin (B) | A = 200 B = 340 | 4.05 ± 0.23 | 10.99 |
| sulcralfate in H$_2$O | 200 | 0.69 ± 0.20* | 84.83 |

*P <0.01 (ANOVA, Tukey test).

From the table V it is evident that by adding a hydrophilic polymer (pectin to the sucralfate) not only the drug activity does not increase but on the contrary is relevantly reduced. This fact is a further evidence of the peculiarity of the interaction between the sulglycotide and said polymers which very probably is strictly related to the fact that both these substances are macromolecules even if, obviously, such an explanation has not limiting sense.

Example of formulation for oral use according to the present invention are now reported.

The pharmaceutical composition for oral use according to the present invention can be prepared in form of tablets and granulates for single dose packages in small envelopes or in form of gels or emulsions.

The daily dosage of the compositions of the invention is of between 200 and 600 mg referred to the amount of sulglycotide.

As regards the pharmaceutical forms in tablets or granulates, the respective amounts of sulglycotide and hydrophilic polymer may vary between 50 and 500 mg.

In the gel the same amounts may vary between 1% and 5% by weight. The ratio between sulglycotide and hydrophilic polymer may vary between 1:1 and 1:5

EXAMPLE 1 gel (% composition)

| | A | B | C |
|---|---|---|---|
| sulglycotide | 1 | 2 | 4 |
| pectin | 3.6 | 3.6 | 3.6 |
| propylene glycol | 4 | 4 | 4 |
| excipients | 20.92 | 20.92 | 20.92 |
| preservants | 0.15 | 0.15 | 0.15 |
| H$_2$O enough to | 100 | 100 | 100 |

EXAMPLE 2 emulsion (% composition)

| | A | B | C |
|---|---|---|---|
| sulglycotide | 1 | 2 | 4 |
| guar gum | 5 | 5 | 5 |
| 70% sorbitol | 74 | 73 | 71 |
| mais oil | 20 | 20 | 20 |

EXAMPLE 3 gel (% composition)

| | |
|---|---|
| sulglycotide | 2 |
| hydroxypropylmethylcellulose | 4 |
| 70% sorbitol | 15 |
| preservants | 0.15 |
| H$_2$ enough to | 100 |

EXAMPLE 4 gel (% composition)

| | |
|---|---|
| sulglycotide | 2 |
| methylcellulose | 1.85 |
| 70% sorbitol | 15 |
| preservants | 0.15 |
| H$_2$O enough to | 100 |

EXAMPLE 5 gel (% composition)

| | |
|---|---|
| sulglycotide | 2 |
| carrageenin | 1.77 |
| preservants | 0.15 |
| 70% sorbital | 15 |
| H$_2$O enough to | 100 |

EXAMPLE 6 gel (% composition)

| | |
|---|---|
| sulglycotide | 2 |
| thragacant gum | 3 |
| 70% sorbitol | 15 |
| preservants | 0.15 |
| H₂O enough to | 100 |

EXAMPLE 7 gel (% composition)

| | |
|---|---|
| sulglycotide | 2 |
| pectin | 3.40 |
| excipients | 11.22 |
| preservants | 0.15 |
| H₂O enough to | 100 |

EXAMPLE 8 masticable or to be sucked tablets (composition in mg)

| | A | B |
|---|---|---|
| sulglycotide | 100 | 200 |
| pectin | 200 | 200 |
| standard excipients enough to | 2000 | 2000 |

EXAMPLE 9 granulates for extemporaneous gel (composition in mg)

| | A | B | C |
|---|---|---|---|
| sulglycotide | 100 | 200 | 400 |
| pectin | 360 | 360 | 360 |
| preservants | 14.4 | 14.4 | 14.4 |
| standard excipients enough to | 3600 | 3600 | 3600 |

We claim:

1. An orally adminstrable composition for the prophylaxis of gastric ulcer comprising a gastroprotective amount of sulglycotide, a hydrophilic polymer selected from the group consisting of methylcellulose, pectin and tragacanth gum, and a pharmaceutically acceptable carrier, and containing between 1:2 and 1:5 parts of sulglycotide per part by weight of the said hydrophilic polymer.

2. A composition according to claim 1, wherein the hydrophilic polymer is methylcellulose.

3. A composition according to claim 2, wherein the hydrophilic polymer is tragacanth gum.

4. A composition according to claim 1, wherein the composition is in the form of a tablet, granulate or a gel.

5. A composition according to claim 4, wherein the tablet or granulate contains between 50 and 500 mg each of sulglycotide and the hydrophilic polymer.

6. A composition according to claim 4, wherein the composition is a gel and contains between 1 and 5% by weight each of sulglycotide and the hydrophilic polymer.

7. A composition according to claim 1, wherein the hydrophilic polymer is pectin.

* * * * *